Figure 1:
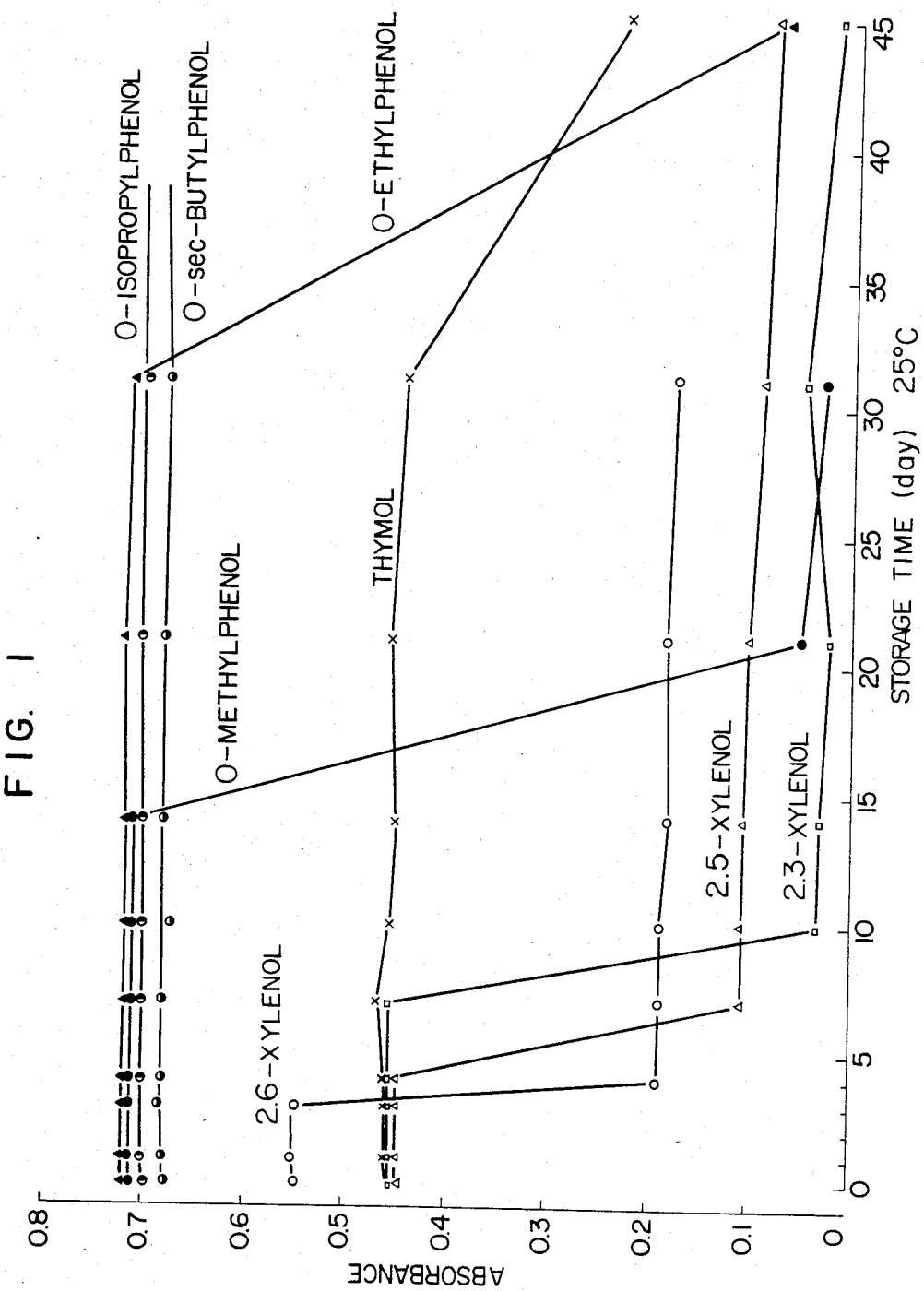

United States Patent [19]

Takabayashi et al.

[11] Patent Number: 4,529,709

[45] Date of Patent: Jul. 16, 1985

[54] METHOD FOR DETERMINATION OF 5-AMINOSALICYLIC ACID

[75] Inventors: Katsuyuki Takabayashi; Muneo Soeta; Takeshi Nagasawa, all of Koriyama, Japan

[73] Assignee: Nitto Boseki Co. Ltd., Fukushima, Japan

[21] Appl. No.: 493,820

[22] Filed: May 12, 1983

[30] Foreign Application Priority Data

May 14, 1982 [JP] Japan .................. 57-81042

[51] Int. Cl.³ .................. G01N 21/78; G01N 33/52
[52] U.S. Cl. .................. 436/111; 435/15; 435/24; 436/904
[58] Field of Search .................. 435/15, 24, 28; 436/111, 66, 904, 135, 131

[56] References Cited

U.S. PATENT DOCUMENTS 3,886,045  5/1975  Meiattini .................. 435/28 X

FOREIGN PATENT DOCUMENTS 0053470  6/1982  European Pat. Off. .
2427327  12/1979  France .
23897    3/1981   Japan .................. 435/15
6164796  12/1981  Japan .................. 435/15

Primary Examiner—Arnold Turk
Attorney, Agent, or Firm—Bert J. Lewen

[57] ABSTRACT

A method for the determination of 5-aminosalicylic acid, which comprises measuring the color developed in an alkaline medium by an oxidative condensation product formed by the condensation of an o-alkylphenol represented by the general formula

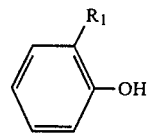

(wherein $R_1$ represents an ethyl, isopropyl or sec-butyl group) with 5-aminosalicylic acid of the formula

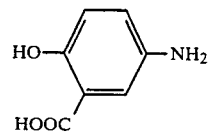

in the presence of a peroxide.

1 Claim, 3 Drawing Figures

METHOD FOR DETERMINATION OF 5-AMINOSALICYLIC ACID

This invention relates to a novel method for the determination of 5-aminosalicylic acid.

The determination of 5-aminosalicylic acid is important in measuring the variation in the amount of such ingredients as γ-GTP, LAP and the like contained in a sample such as the blood of a biological specimen, by using a novel substrate having 5-aminosalicylic acid as a color forming group, said substrate having been developed for the purpose of providing reference data for the clinical diagnosis.

The substrate which has heretofore been generally used in the determination of γ-GTP or LAP is L-γ-glutamyl p-nitroanilide (for the determination of γ-GTP) or L-leucyl p-nitroanilide (for the determination of LAP). These substrates, however, offer problems such as solubility of the substrate and the influence of serum ingredients on the colorimetric determination of liberated yellow p-nitroaniline. In order to solve such problems, there have been developed new substrates such as L-γ-glutamyl 3-carboxy-4-hydroxyanilide (Japanese Patent Publication No. 49,904/81) and L-leucyl 3-carboxy-4-hydroxy anilide (Japanese Patent Publication No. 30,341/81). In determining γ-GTP and LAP by use of these new substrates, it is necessary to allow the liberated 5-aminosalicylic acid to react with a coupler to form a color substance (coloring matter) which can be colorimetrically determined.

The requirements for the color substance formed by the oxidative condensation of a coupler and the 5-aminosalicylic acid which is liberated by the reaction of a substrate with an enzyme of living bodies are such that it should exhibit an absorption maximum ($\lambda_{max}$) at 600 nm or longer wave lengths so as to avoid the influence of coexisting coloring matters such as bilirubin (absorption maximum at 450 nm) and hemoglobin (absorption maximum at 550 nm), which are typical of the coloring matters contaminating the biological specimens, and that it should have a high coloration sensitivity (high molar extinction coefficient $\epsilon$).

The color reagent solution is required to be free of the deterioration in color developing ability with time, that is, to be capable of maintaining its color developing ability for a period as long as at least 20 days, preferably 30 days or more at room temperature without showing any change such as discoloration. The couplers generally used heretofore as most desirable ones are 2,3-xylenol, 2,5-xylenol, 2,6-xylenol, thymol and o-methylphenol. These couplers, however, have disadvantages in that the deterioration with time in color developing ability is great during storage at ordinary temperatures. This is particularly marked in the case of xylenols, most of which lose the color developing ability in 5 to 7 days, and even o-methylphenol, which while remaining stable for a longer period of time, deteriorates when stored for a period exceeding 15 days. Furthermore, the phenols show discoloration (yellow to brown) in the presence of peroxides such as sodium metaperiodide, which detracts much from their commercial values.

The present inventors, in consideration of the above disadvantages, made an extensive study to develop a color developing solution which is not deteriorated in color developing ability and, as a result, found that o-ethylphenol, o-isopropylphenol, and o-sec-butylphenol are couplers which meet the requirements for the desirable couplers. When used in a color developing solution, these phenols show a much more stable color developing ability with substantially no discoloration, as compared with already known couplers.

The color reaction can be conducted in a known way as shown, for example by the following schedule in which the 5-aminosalicylic acid (I) liberated from a substrate by the enzymatic reaction is allowed to condense oxidatively with a coupler (II) in an alkaline medium to form a color substance (III) which is colorimetrically determined. A peroxide salt such as sodium or potassium metaperiodate is used as an oxidizing agent in the oxidative condensation.

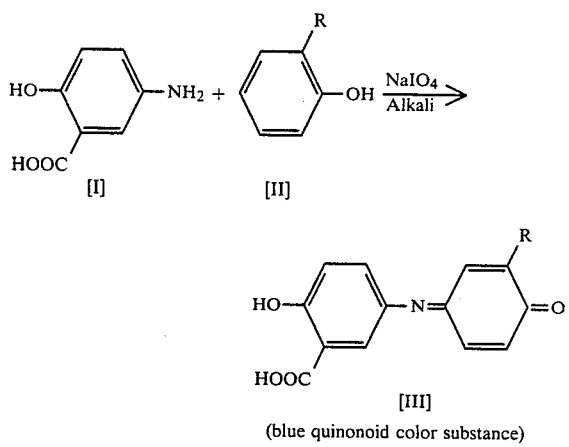

(blue quinonoid color substance)

The features of a color reagent solution, in which the coupler of this invention is used, are illustrated with reference to accompanying drawings.

FIG. 1 presents the results of test (at 25° C.) for the color developing ability of color reagents.

Figure 2:
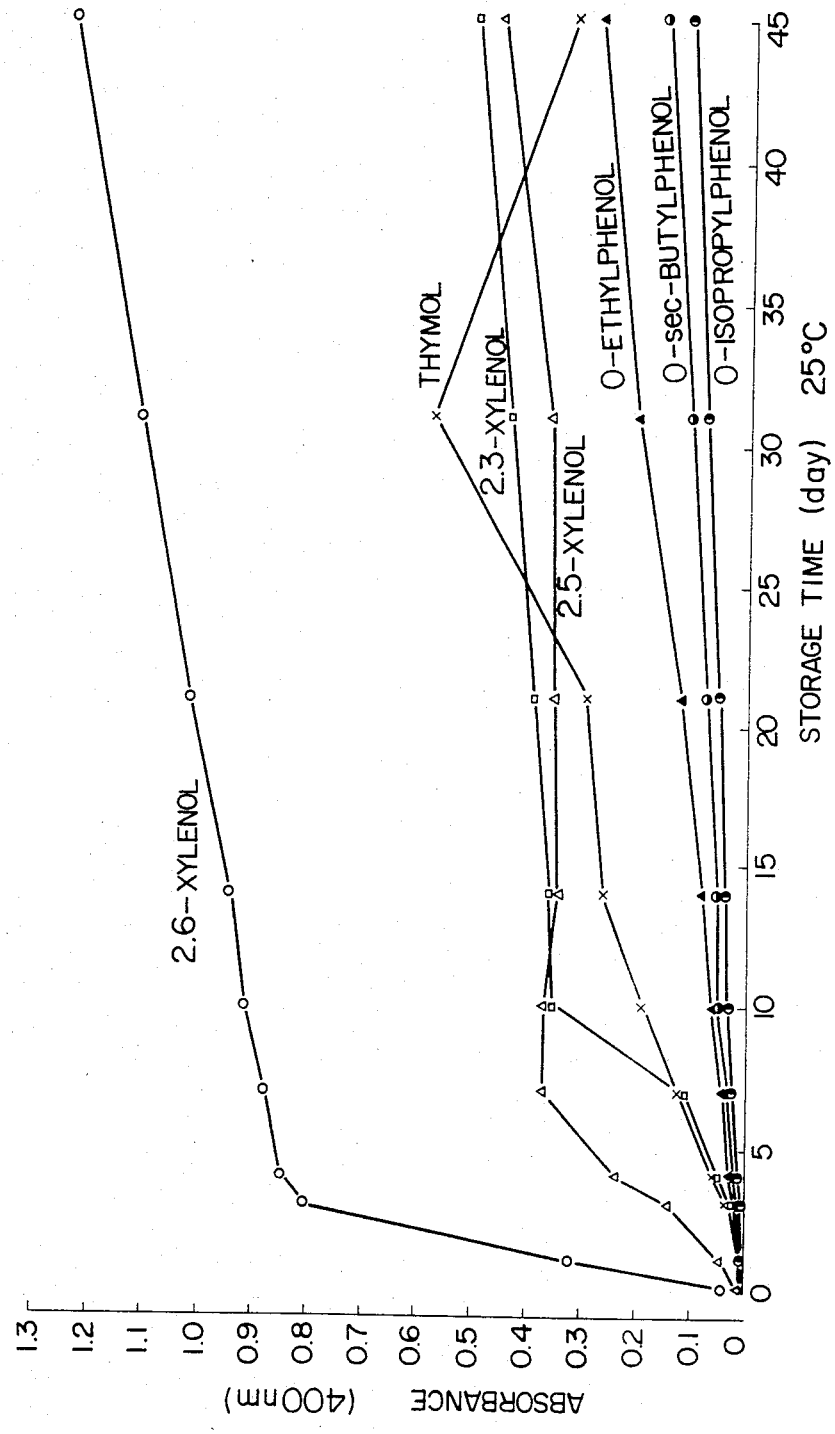
Figure 3:
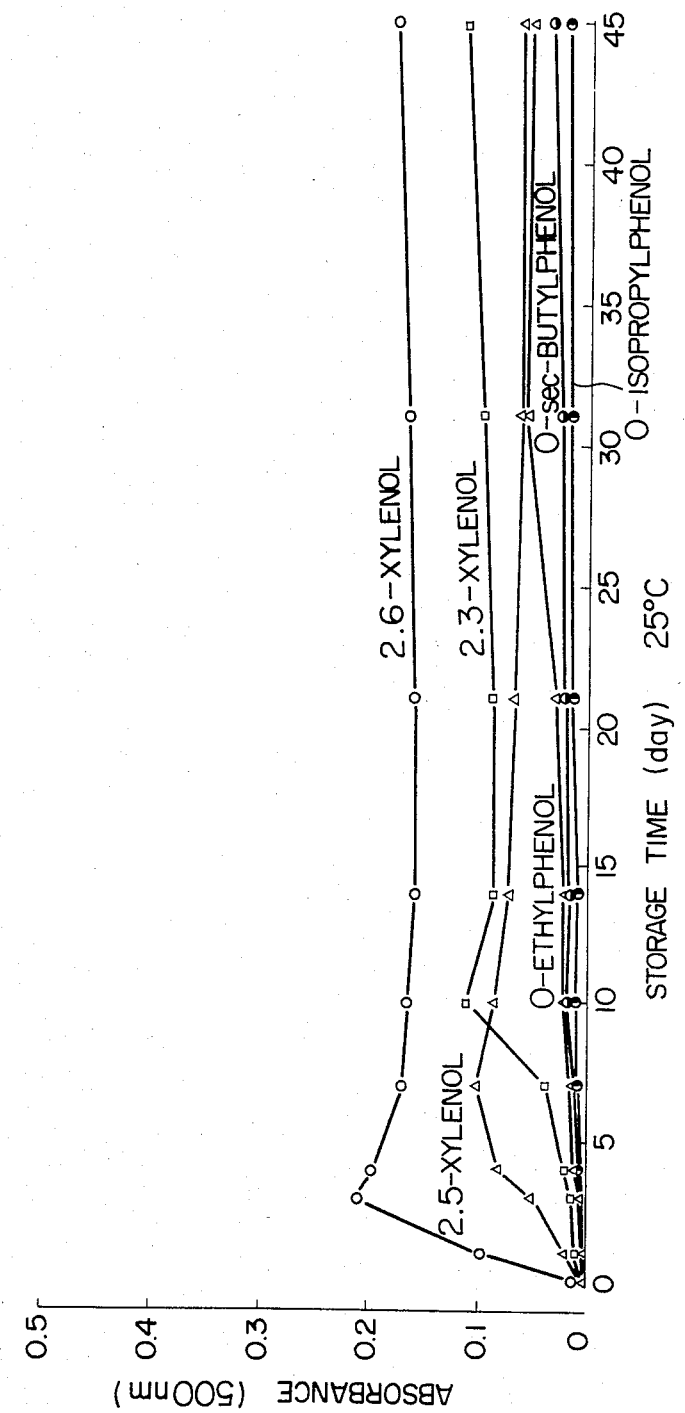

FIGS. 2 and 3 show the change with time of storage in the developed color at 400 nm in the yellow region and at 500 nm in the red region, respectively.

EXAMPLE 1

Test for the change with time in color developing ability of a color reagent solution.

(1) Color reagent solution: A color reagent solution was prepared by dissolving 7 mM of a coupler (a phenol) and 1.5 mM (0.32 g) of sodium metaperiodate in 1,000 ml of 0.2-N aqueous potassium hydroxide solution.

(2) Standard solution: A standard solution was prepared by dissolving 0.1 mM (0.0189 g) of 5-aminosalicylic acid hydrochloride in 1,000 ml of purified water.

Test for the change with time in color developing ability of each color reagent solution: The above color reagent solution was stored at 25° C. and the color developing ability was tested at predetermined time intervals in the following manner:

The color reagent solution (3 ml) and the standard solution (1 ml) were thoroughly mixed and allowed to react at 25° C. for 10 minutes. The adsorbance of the reaction mixture was measured at the wave length of absorption maximum by means of a spectrophotometer. The results of test were as shown in FIG. 1. In Table 1, there were shown the absorption maximum ($\lambda_{max}$) and the molar extinction coefficient of each color reagent solution immediately after preparation.

As known from FIG. 1, when stored at 25° C. xylenols lose the color developing ability in about one week, and further, even o-methylphenol which has been considered to be good loses the color developing ability in two weeks. As compared with the conventional ones, the couplers found by the present inventors show to have a stable color developing ability for a period as long as more than thirty days even in o-ethylphenol and as more than forty-five days in o-isopropylphenol and o-sec-butylphenol, and further, to have a remarkably high coloration sensitivity.

EXAMPLE 2

Stability of the color reagent solution.

(1) Color reagent solution: The same as that in Example 1.

The color reagent solution was stored at 25° C. and the degree of discoloration was measured at predetermined time intervals to test the stability of the reagent solution. The test was performed by measuring the absorbance at 400 nm (yellow region) and 500 nm (red region) at predetermined time intervals to examine the degree of discoloration. The test results were as shown in FIGS. 2 and 3.

As is apparent from both FIGS. 2 and 3, in the case of xylenols, a marked discoloration took place in one week even in the case of a compound of better preservability and in one day in the case of a compound of particularly worse preservability. The discoloration resulted in an increase in the value of blank test and interferes with the colorimetric measurement. The couplers of the present inventors showed only an increase as slight as not sensible of coloring to naked eye in the value of blank test during at least two weeks under the conditions of test, offering a proof for the advantage of the couplers of this invention.

TABLE 1

| | Blue quinonoid color substance (III) | |
|---|---|---|
| Compound (II) | $\lambda_{max}$ (nm) | Molar extinction coeff. $\epsilon$ (M$^{-1}$ cm$^{-1}$) |
| o-Ethylphenol | 645 | 28710 |
| o-Isopropylphenol | 645 | 27800 |
| o-sec-Butylphenol | 645 | 26950 |

TABLE 1-continued

| | Blue quinonoid color substance (III) | |
|---|---|---|
| Compound (II) | $\lambda_{max}$ (nm) | Molar extinction coeff. $\epsilon$ (M$^{-1}$ cm$^{-1}$) |
| (Reference) 2,3-Xylenol | 640 | 18180 |
| 2,5-Xylenol | 635 | 17840 |
| 2,6-Xylenol | 610 | 21610 |
| Thynol | 635 | 18080 |

Experimental procedure:
Standard solution: 1 ml
Color reagent solution: 3 ml
The absorbance was measured at 25° C. and 10 minutes after mixing.
Standard solution: 0.1 mM 5-aminosalicylic acid.
Color reagent solution:

7 mM coupler
1.5 mM NaIO$_4$ } in 0.2-N KOH solution

What is claimed is:

1. A method for the determination of 5-aminosalicylic acid, which comprises measuring the color developed in an alkaline medium by an oxidative condensation product formed by the condensation of an o-alkylphenol represented by the general formula

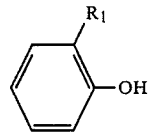

(wherein R$_1$ represents an ethyl, isopropyl or sec-butyl group) with 5-aminosalicylic acid of the formula

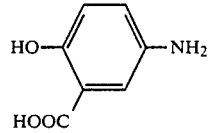

in the presence of a peroxide.

* * * * *